United States Patent [19]

Inazu et al.

[11] Patent Number: 5,317,029

[45] Date of Patent: May 31, 1994

[54] PHARMACEUTICAL COMPOSITION OF BENZOPYRANES FOR THE INHIBITION OF BONE RESORPTION

[75] Inventors: Mizuho Inazu; Ryoichi Satoh; Tsutomu Inoue, all of Saitama; Hiroshi Kitagawa, Kawajima; Masakazu Katoh, Saitama, all of Japan; Heinrich Englert, Hofheim am Taunus, Fed. Rep. of Germany; Denis Carniato, Clamart, France; Hans-Jochen Lang, Hofheim am Taunus, Fed. Rep. of Germany

[73] Assignee: Hoechst Japan Limited, Tokyo, Japan

[21] Appl. No.: 990,617

[22] Filed: Dec. 14, 1992

[30] Foreign Application Priority Data

Dec. 16, 1991 [JP] Japan ................................ 3-331767
Sep. 8, 1992 [JP] Japan ................................ 4-239144

[51] Int. Cl.⁵ ................... A61K 31/44; A61K 31/53; A61K 31/35
[52] U.S. Cl. ..................... 514/422; 514/336; 514/345; 514/424; 514/456; 514/457; 514/337
[58] Field of Search ............... 514/410, 411, 413, 456, 514/457, 337, 422

[56] References Cited

FOREIGN PATENT DOCUMENTS 0093535 11/1983 European Pat. Off. .
0207614 1/1987 European Pat. Off. .
0350805 1/1990 European Pat. Off. .
58-67683 4/1983 Japan .
58-188880 11/1983 Japan .
58-219183 12/1983 Japan .
63-201182 8/1988 Japan .

OTHER PUBLICATIONS

Buckle et al., J. Med. Chem., vol. 33, 1990, pp. 3028-3034.
Lodge et al., J. Pharmacol. Exp. Ther., vol. 256, No. 2, pp. 639-644, 1991.
Paciorek et al., J. Cardiovasc. Pharmacol., vol. 15, No. 2, pp. 188-197, 1990
Hamilton et al., Br. J. Pharmacol., vol. 88, pp. 103-111, 1986.

Sassen et al., Br. J. Pharmacol., vol. 101, pp. 605-614, 1990.

*Primary Examiner*—Frederick E. Waddell
*Assistant Examiner*—T. J. Criares
*Attorney, Agent, or Firm*—Finnegan, Henderson, Farabow, Garrett & Dunner

[57] ABSTRACT

Pharmaceutical compositions for the inhibition of bone resorption comprising a pharmaceutical carrier and a therapeutically effective amount of a benzopyran derivative represented by the general formula (I)

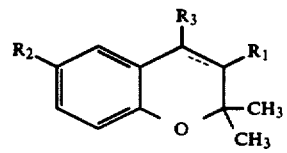

wherein the broken-lined bond denotes an optional double bond, $R_1$ denotes a hydrogen atom or a hydroxyl group, $R_2$ denotes a cyano group, a phenylsulfonyl group or a halogen-substituted methoxyl group, and $R_3$ denotes a group having the formula

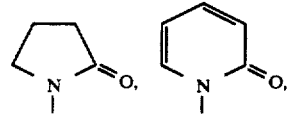

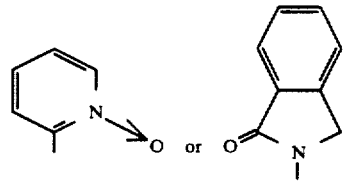

Since they inhibit bone resorption, they are useful for the treatment and prevention of diseases associated with bone metabolism.

6 Claims, No Drawings

PHARMACEUTICAL COMPOSITION OF BENZOPYRANES FOR THE INHIBITION OF BONE RESORPTION

BACKGROUND OF THE INVENTION

1. Field of the Invention

This invention relates to novel pharmaceutical compositions for preventing or treating diseases involving abnormal decreases in calcium and bone matrix from the bone (bone resorption). Abnormal bone resorption occurs not only in osteoporosis but also in rheumatoid arthritis, Paget disease, bone metastasis of malignant tumor, hyperthyroidism, or post-oophorectomy state. In addition, it is associated with neural excision or prolonged disuse or fixation of the extremities. As a result, fragility of bone and risk of fracture are increased. Moreover, it is estimated that patients with such diseases, particularly, osteoporotic patients will increase as the population of elderly people aged 65 years or more rapidly grows in Japan owing to the prompt prolongation of the Japanese' average life span. The term "osteoporosis" as used in the present specification refers to senile osteoporosis and postmenopausal osteoporosis.

2. Description of the Prior Art

Pharmaceutical compositions including vitamin $D_3$, calcitonin, estrogens and bisphosphonate derivatives have been used in clinical practice. Their therapeutic results, however, are not entirely satisfactory, and a better pharmaceutical composition is highly desired.

SUMMARY OF THE INVENTION

Bone resorption is known to occur upon activation of osteoclasts. We have made extensive studies to find a pharmaceutical composition that selectively inhibits osteoclasts with high safety. We have discovered that a series of benzopyran derivatives represented by the general formula (I)

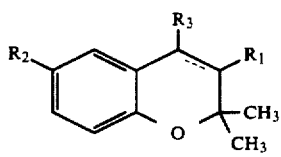

inhibit bone resorption. This discovery led us to accomplish the present invention.

This invention is directed to pharmaceutical compositions for the inhibition of bone resorption comprising a pharmaceutical carrier and a therapeutically effective amount of a benzopyran derivative represented by the general formula (I)

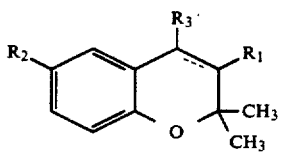

wherein the broken-lined bond denotes an optional double bond, $R_1$ denotes a hydrogen atom or a hydroxyl group, $R_2$ denotes a cyano group, a phenylsulfonyl group or a halogen-substituted methoxyl group, and $R_3$ denotes a group having the formula

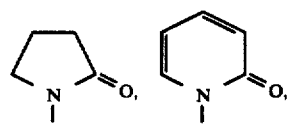

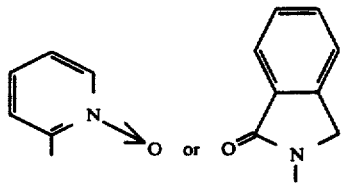

Examples of the benzopyran derivative are as follows:

| Compound | $R_1$ | | $R_2$ | $R_3$ |
|---|---|---|---|---|
| I | —OH (trans to $R_3$) | Single bond | ![phenylsulfonyl] | ![pyrrolidinone] |
| II | —OH (trans to $R_3$) | Single bond | N≡C— | " |
| III | —H | Double bond | " | ![pyridinone] |
| IV | —H | Double bond | " | ![pyridinone isomer] |
| V | —OH (trans to $R_3$) | Single bond | $F_3CO—$ | ![isoindolinone] |

This invention is also directed to the use of a therapeutically effective amount of a benzopyran derivative represented by the formula I for the production of a pharmaceutical composition for the inhibition of bone resorption.

All of these benzopyran derivatives are known compounds. For example, Compound I is described in Japanese Laid-Open Patent Publication No. 201182/1988, Compound II in Br. J. Pharmacol., vol. 88, pp. 103-111 (1986) and Japanese Laid-Open Patent Publication Nos. 67683/1983, 188880/1983 and 219183/1983, Compound III in Br. J. Pharmacol., vol. 101, pp. 605-614(1990), Compound IV in J. Cardiovasc. Pharmacol., vol. 15, pp. 188-197 (1990), and Compound V in J. Pharmacol. Exp. Ther., vol. 256, pp. 639-644(1991). Acute toxicity studies on Compound I have shown that its $LD_{50}$ is 470 mg/kg (p.o.) and 103 mg/kg (i.v.) in mice; it is about 2,000 mg/kg (p.o.) and 128 mg/kg (i.v.) in rats. Thus, the toxicity of this compound is relatively weak.

The compound of the present invention is useful for a pharmaceutical composition for the inhibition of bone resorption. It can be administered parenterally as subcutaneous injections, intravenous injections or intramuscular injections, or orally as tablets, capsules, granules, powders or syrup.

The dose of the compound according to the present invention varies with the route of administration, the age, body weight, symptoms of the patient, etc. Its daily dose for adults is 1-200 mg, desirably 10-100 mg.

The pharmaceutical composition of the present invention comprises a therapeutically effective amount of a benzopyran derivative represented by formula I and a pharmaceutically acceptable carrier.

The compound of the present invention is made into the above-mentioned formulations using ordinary adjuvants, such as fillers, disintegrators, binders, lubricants, or perfumes. It may also be bound to a compound, protein or peptide with a high affinity for a bone tissue so as to provide a dosage form for specific penetration into the bone tissue.

The bone resorption inhibitor action of the compound according to the invention is demonstrated in vitro based on its direct effect on the activity of osteoclasts, and in vivo based on its effects in rats with experimental hypercalcemia and in rats with bone atrophy due to experimental immobility.

The in vitro effect on osteoclastic activity can be examined by, say, pit formation assay. According to this method, a small ivory piece (about 6 mm in diameter) with a microscopically smooth surface is added to a suspension of murine bone marrow cells including osteoclasts. Parathyroid hormone (PTH) is further added to activate the osteoclasts. The activated osteoclasts lyse the mineral and proteinous matrix on the small ivory piece to form pits. The present compound is added to this test liquid, and the number of pits on the small ivory piece caused by the osteoclasts induced bonelysis is counted to determine the efficacy of the present compound. The higher the bone resorption inhibitor effect of the compound is, the fewer pits are formed. Calcitonin is used as a positive control.

In an in vivo test, the systemic effect of the present compound can be investigated. PTH is known to increase serum calcium ion levels. Thus, the administration of PTH can induce hypercalcemia experimentally. The effect of the present compound on the blood calcium ion levels in rats with so induced hypercalcemia can be used as a parameter in determining its bone metabolism improving activity.

The bone resorption inhibitory action of the present compound can also be examined in models with bone atrophy due to experimental disuse. Rigid dressings after fracture and immobility ascribed to traumatic excision of a nerve are known to impair the balance between bone resorption and bone formation in favor of the former, thereby decreasing bone mass. Experimental resection of the brachial nerve in the axillary region results in bone atrophy due to decreases in the bone mass of the ulna and radius (on a dry weight basis) resulting from the disuse of the arm. The efficacy of the present compound against this type of atrophy can be determined by calculating the ratio of the bone mass of the ulna and radius on the resected side to that on the non-resected side.

EXAMPLES

The effects of the present invention will be described in more detail by reference to the following Examples.

EXAMPLE 1

In Vitro Inhibition of Bone Resorption

Bone marrow cells were collected from the long bone of a 10 days old ICR mouse. Broken pieces of the bone were removed by centrifugal separation in an MEM medium containing 5% bovine fetal serum. The bone marrow cells were re-suspended in the same medium to a cell density of $10^7$/ml. The suspension was added in a volume of 100 μl per well to a 96-well plate. Each well of the plate had a small ivory piece with a diameter of 6 mm placed therein. A test drug was added to the cell suspension to a concentration of $1 \times 10^{-6}$ to $1 \times 10^{-10}$ mol. The plate was incubated for 3 days at 37° C. in the presence of $1 \times 10^{-7}$ mol of PTH. The ivory pieces were then removed, stained with coomassie brilliant blue, and measured under the microscope for the number of pits formed. The number of the pits in the group receiving the test drug was compared with that in the group given no test drug, and the difference was statistically analyzed by Student's t-test. The results are shown in Table 1.

The increase in the number of the pits prompted by PTH was significantly inhibited (p<0.01) by commercially available eel calcitonin (hereinafter referred to as eCT) at a concentration of $1 \times 10^{-8}$ mol, by Compound I at a concentration of $1 \times 10^{-8}$ mol, and by Compound II at a concentration of $1 \times 10^{-6}$ mol. eCT was used as a positive control.

TABLE 1

| Test drug | PTH concentration (mol) | Test drug concentration (mol) | Number of pits |
|---|---|---|---|
| Control group (PTH−) | 0 | 0 | 55.50 ± 44.52 |
| Control group (PTH+) | 1 × 10⁻⁷ | 0 | 200.33 ± 33.81 |
| eCT | 1 × 10⁻⁷ | 1 × 10⁻⁸ | 92.22 ± 39.60** |
| Compound I | 1 × 10⁻⁷ | 1 × 10⁻⁶ | 81.17 ± 41.41** |
| Compound I | 1 × 10⁻⁷ | 1 × 10⁻⁸ | 100.00 ± 47.14** |
| Compound I | 1 × 10⁻⁷ | 1 × 10⁻¹⁰ | 191.17 ± 87.27 |
| Control group (PTH−) | 0 | 0 | 71.50 ± 24.12 |
| Control group (PTH+) | 1 × 10⁻⁷ | 0 | 216.50 ± 48.23 |
| eCT | 1 × 10⁻⁷ | 1 × 10⁻⁸ | 99.56 ± 52.92** |
| Compound II | 1 × 10⁻⁷ | 1 × 10⁻⁶ | 129.50 ± 22.35** |
| Compound II | 1 × 10⁻⁷ | 1 × 10⁻⁸ | 167.67 ± 66.41 |
| Compound II | 1 × 10⁻⁷ | 1 × 10⁻¹⁰ | 220.83 ± 81.76 |

Means ± standard deviations
**Significantly different from the control group (PTH+) at p <0.01

EXAMPLE 2

Efficacy in models with hypercalcemia (Run 1)

Five-week old male SD rats were not fed for 20 hours. Then, they were divided into groups of 3 to 5 animals, and intravenously administered 60 U/kg of human PTH (N1-34) to establish hypercalcemia. The test drug was dissolved in physiological saline, and the solution was intravenously administered 15 minutes before the administration of PTH. The control groups received physiological saline similarly. Blood samples were taken 60 minutes after the administration of PTH, and the serum calcium ion levels were measured. The values were compared between the control groups and the groups given the test drug, and the differences were statistically analyzed by Student's t-test.

The results are shown in Table 2. The administration of PTH significantly increased the serum calcium ion levels, showing that hypercalcemia was induced. The minimal effective dose for inhibiting this abnormality was 0.1 mg/kg for Compound I and 1.0 mg/kg for Compound II.

TABLE 2

| Test drug | Dose of test drug (mg/kg) | Serum $Ca^{++}$ level (mmol/l) |
|---|---|---|
| Control group (PTH−) | 0 | 1.36 ± 0.01** |
| Control group (PTH+) | 0 | 1.44 ± 0.01 |
| Compound I | 0.1 | 1.37 ± 0.02** |
|  | 1.0 | 1.39 ± 0.03** |
| Compound II | 0.3 | 1.43 ± 0.03 |
|  | 1.0 | 1.34 ± 0.03** |

Means ± standard deviations
**Significantly different from the control group (PTH+) at $p < 0.01$.

EXAMPLE 3

Efficacy in Models with Hypercalcemia (Run 2)

Five-week old male SD rats were not fed for 20 hours. Then, they were divided into groups of 4 or 5 animals, and intravenously administered 30 μg/kg of human PTH (N1-34) to establish hypercalcemia. The test drug was dissolved in physiological saline, and the solution was intravenously administered 15 minutes before the administration of PTH. The control groups received physiological saline similarly. Blood samples were taken 60 minutes after the administration of PTH, and the serum calcium ion levels were measured. The values were compared between the control groups and the groups given the test drug, and the differences were statistically analyzed by Student's t-test.

The results are shown in Table 3. The administration of PTH significantly increased the serum calcium ion levels, showing that hypercalcemia was induced. The minimal effective dose for inhibiting this abnormality was 0.3 mg/kg for Compound III and 0.1 mg/kg or less for Compound IV.

TABLE 3

| Test drug | Dose of test drug (mg/kg) | Serum $Ca^{++}$ level (mmol/l) |
|---|---|---|
| Control group (PTH−) | 0 | 1.45 ± 0.02** |
| Control group (PTH+) | 0 | 1.51 ± 0.03 |
| Compound III | 0.1 | 1.47 ± 0.05 |
|  | 0.3 | 1.45 ± 0.04* |
|  | 1.0 | 1.42 ± 0.02** |
| Compound IV | 0.1 | 1.43 ± 0.03** |
|  | 0.3 | 1.45 ± 0.03** |
|  | 1.0 | 1.44 ± 0.02** |

Means ± standard deviations.
**Significantly different from the control group (PTH+) at $p < 0.01$.
*Significantly different from the control group (PTH+) at $p < 0.05$.

EXAMPLE 4

Efficacy in Models with Bone Atrophy Due to Immobility

The brachial nerve was resected from the left axillary region in male SD rats (six-week old) under pentobarbital anesthesia to establish immobility-associated bone atrophy models. They were divided into groups of 5 or 6 animals, and immediately after the resection, were intravenously administered Compound I in a dose of 1.0 mg/kg twice daily for 1 or 2 weeks, and Compound II in a dose of 1.0 mg/kg twice daily for 1 week. The control groups were similarly administered physiological saline twice daily for 1 or 2 weeks by the intravenous route. Then, the radius and the ulna were removed, dehydrated and defatted with alcohol. Thereafter, these bones were dried for 6 hours at 160° C., and their weights were measured. The ratio of the weight of the left ulna to that of the right ulna, as well as the ratio of the weight of the left radius to that of the right radius were calculated. The values were compared between the control group and each treated group, and the differences were statistically analyzed by Student's t-test.

The results are shown in Table 4. When administered for one week, Compound II significantly inhibited the decrease in the weight of the ulna on the denervated side, while Compound I tended to inhibit this decrease, although not significantly. Following two weeks of treatment, Compound I significantly inhibited the decreases in the weights of the ulna and the radius on the denervated side.

TABLE 4

| Test drug | Dose of test drug (mg/kg) | Treatment period | Left bone/right bone dry weight ratio Ulna | Radius |
|---|---|---|---|---|
| Control group | 0 | 1 week | 0.930 ± 0.013 | 0.969 ± 0.015 |
| Compound I | 1.0 |  | 0.950 ± 0.020 | 0.965 ± 0.031 |
| Compound II | 1.0 |  | 0.966 ± 0.019** | 0.989 ± 0.034 |
| Control group | 0 | 2 week | 0.910 ± 0.020 | 0.909 ± 0.008 |
| Compound I | 1.0 |  | 0.942 ± 0.010** | 0.939 ± 0.023* |

Means ± standard deviations.
**Significantly different from the control group (PTH+) at $p < 0.01$.
*Significantly different from the control group (PTH+) at $p < 0.05$.

A formulation of the present invention will be described by way of the following example.

FORMULATION EXAMPLE

Distilled water for injection was added to 0.4 g of Compound I and 16 g of sodium chloride to make a total 2,000 ml liquid. This liquid was sterile-filtered through a 0.22 micron Millipore filter, and dispensed in a volume of 5 ml each to ampoules with a capacity of 5 ml. The ampoules were melt-sealed, and autoclave-sterilized to obtain injections.

As clearly seen from the above description, the compounds according to the present invention show in vitro inhibition of bone resorption, in vivo correction of abnormal bone metabolism in animal models with experimental hypercalcemia and with bone atrophy due to experimental immobility. Thus, these compounds are suggested to alleviate diseases associated with bone metabolism, such as osteoporosis and hypercalcemia.

What is claimed is:

1. A method for treating bone resorption which comprises administering an effective amount for said treatment of a benzopyran derivative represented by formula (I)

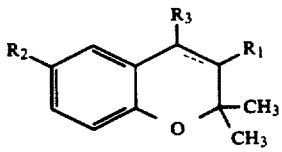

wherein the broken-lined bond denotes an optional double bond, $R_1$ denotes a hydrogen atom or a hydroxyl group, $R_2$ denotes a cyano group, a phenylsulfonyl group or a halogen-substituted methoxyl group, and $R_3$ denotes a group having the formula

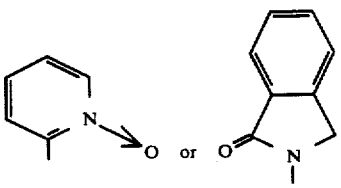

together with a pharmaceutically acceptable carrier.

2. The method of claim 4 wherein $R_1$ denotes a hydroxyl group, $R_2$ denotes a cyano group, $R_3$ denotes a 2-oxo-1-pyrrolidinyl group in trans position to $R_1$, and the broken-lined bond denotes a single bond.

3. The method of claim 4 wherein $R_1$ denotes a hydroxyl group, $R_2$ denotes a phenylsulfonyl group, $R_3$ denotes a 2-oxo-1-pyrrolidinyl group in trans position to $R_1$, and the broken-lined bond denotes a single bond.

4. The method of claim 4, wherein said effective amount is a daily dosage of from 1 to 200 mg for adults.

5. The method of claim 4, wherein said effective amount is a daily dosage of from 10 to 100 mg for adults.

6. The method of claim 4, wherein said benzopyran derivative is administered parenterally or orally.

* * * * *

UNITED STATES PATENT AND TRADEMARK OFFICE
CERTIFICATE OF CORRECTION

PATENT NO. : 5,317,029
DATED : May 31, 1994
INVENTOR(S) : Mizuho INAZU et al.

It is certified that error appears in the above-indentified patent and that said Letters Patent is hereby corrected as shown below:

Claim 2, column 8, line, 12;

Claim 3, column 8, line, 16;

Claim 4, column 8, line, 20;

Claim 5, column 8, line, 22; and

Claim 6, column 8, line, 24 change "Claim 4" to --Claim 1--.

Signed and Sealed this

Fourteenth Day of March, 1995

Attest:

BRUCE LEHMAN

*Attesting Officer*          *Commissioner of Patents and Trademarks*